US012667326B2

(12) United States Patent (10) Patent No.: US 12,667,326 B2
Wei et al. (45) Date of Patent: Jun. 30, 2026

(54) HYBRID RING-TYPE SMART STETHOSCOPE AND METHOD FOR PRODUCING SAME

(71) Applicant: INDUSTRY ACADEMIC COOPERATION FOUNDATION KEIMYUNG UNIVERSITY, Daegu (KR)

(72) Inventors: Qun Wei, Daegu (KR); Hee Joon Park, Daegu (KR)

(73) Assignee: INDUSTRY ACADEMIC COOPERATION FOUNDATION KEIMYUNG UNIVERSITY, Daegu (KR)

( * ) Notice: Subject to any disclaimer, the term of this patent is extended or adjusted under 35 U.S.C. 154(b) by 347 days.

(21) Appl. No.: 18/286,960

(22) PCT Filed: Apr. 6, 2022

(86) PCT No.: PCT/KR2022/004933
§ 371 (c)(1),
(2) Date: Oct. 13, 2023

(87) PCT Pub. No.: WO2022/220475
PCT Pub. Date: Oct. 20, 2022

(65) Prior Publication Data
US 2024/0197285 A1 Jun. 20, 2024

(30) Foreign Application Priority Data

Apr. 14, 2021 (KR) ......................... 10-2021-0048196

(51) Int. Cl.
*A61B 7/04* (2006.01)
*A61B 5/0205* (2006.01)
*A61B 7/00* (2006.01)
(52) U.S. Cl.
CPC .............. *A61B 7/04* (2013.01); *A61B 5/0205* (2013.01); *A61B 7/003* (2013.01);
(Continued)

(58) Field of Classification Search
CPC ......... A61B 7/04; A61B 5/0205; A61B 7/003; A61B 2560/0425; A61B 2560/0443;
(Continued)

(56) References Cited

U.S. PATENT DOCUMENTS 5,471,983 A * 12/1995 Magnus ................. A61B 5/256
607/149
6,202,784 B1 3/2001 Alatriste
(Continued)

FOREIGN PATENT DOCUMENTS

JP 2008-018148 A 1/2008
JP 2008-206857 A 9/2008
(Continued)

*Primary Examiner* — Jason Chan
(74) *Attorney, Agent, or Firm* — Bridgeway IP Law Group, PLLC; Sang Ho Lee; Hyun Woo Shin

(57) ABSTRACT

Provided is a hybrid ring-type smart stethoscope and a method for producing the same, and the hybrid ring-type smart stethoscope includes: a connection part which has a hollow hole into which a user's finger is inserted; an upper structure which is provided on the top of the connection part; and a lower structure which is provided on the bottom of the connection part, and has a measurement module collecting body-related information, which includes the user's heartbeat or respiratory information, by coming into contact with the user. The method of producing a hybrid ring-shaped smart stethoscope includes the steps of: preparing a connection part for wearing on a user's finger; installing an upper structure on the top of the connection part in a foldable manner; and installing a lower structure on the bottom of the connection part in a foldable manner. Therefore, the hybrid ring-type smart stethoscope can effectively auscultate a user's pulse and cardiopulmonary sounds, and is conveniently portable on an ordinary day.

17 Claims, 16 Drawing Sheets

(52) U.S. Cl.
　　CPC ................. *A61B 2560/0425* (2013.01); *A61B*
　　　　　　　　*2560/0443* (2013.01); *A61B 2562/12*
　　　　　　　　(2013.01); *A61B 2562/18* (2013.01)

(58) Field of Classification Search
　　CPC ............ A61B 2562/12; A61B 2562/18; A61B
　　　　　　　5/02438; A61B 5/6826; A61B 2562/0204;
　　　　　　　A61B 7/00; A61B 7/02; A61B 5/0002;
　　　　　　　A61B 5/02208; A61B 5/02241; A61B
　　　　　　　5/6844; A61B 5/746; A61B 2562/16
　　See application file for complete search history.

(56) References Cited

U.S. PATENT DOCUMENTS

2002/0147404 A1\* 10/2002 Kato ...................... A61B 5/681
　　　　　　　　　　　　　　　　　　600/503
2006/0247670 A1\* 11/2006 LeVaughn .......... A61B 5/15117
　　　　　　　　　　　　　　　　　　606/181

2014/0051962 A1\* 2/2014 Krusor ................ A61B 5/7405
　　　　　　　　　　　　　　　　　　600/386
2018/0020937 A1\* 1/2018 Chou .................... A61B 5/291
　　　　　　　　　　　　　　　　　　600/301
2021/0037932 A1\* 2/2021 Min .................... A61B 5/0006

FOREIGN PATENT DOCUMENTS

| | | | |
|---|---|---|---|
| JP | 2013-085559 A | 5/2013 | |
| JP | 2017-000198 A | 1/2017 | |
| JP | 3217016 U | 7/2018 | |
| KR | 10-2014-0135203 A | 11/2014 | |
| KR | 10-1957110 B1 | 3/2019 | |
| KR | 1957110 B1 \* | 3/2019 | .......... A61B 5/0024 |
| KR | 102472365 \* | 10/2020 | .............. A61B 7/04 |
| KR | 10-2020-0124990 A | 11/2020 | |
| WO | WO-2012013350 A1 \* | 2/2012 | .......... A61B 5/6826 |

\* cited by examiner

HYBRID RING-TYPE SMART STETHOSCOPE AND METHOD FOR PRODUCING SAME

TECHNICAL FIELD

The present invention relates to a hybrid ring-type smart stethoscope and a method for producing the same, and more specifically, to a hybrid ring-type smart stethoscope which can effectively auscultate a user's pulse and cardiopulmonary sounds, and is conveniently portable on an ordinary day, and a method for producing the same.

BACKGROUND ART

In general, a stethoscope is used to listen to internal sounds such as heartbeats, breath sounds, arterial sounds, bowel sounds, and vascular sounds to check if they are in a normal state, and is used to listen to auscultate the brachial arterial sound when measuring blood pressure.

Such stethoscopes are designed and placed in a uniform shape for medical examination, but a user who performs medical examination cannot always carry and use the stethoscopes.

Moreover, even if the user tries to intentionally carry the stethoscope, there is an inconvenience due to the shape of the stethoscope, and there is a risk of loss and damage.

Therefore, there is a pressing need for technological development regarding a hybrid ring-type smart stethoscope which is convenient for carrying and keeping, and provides convenience in use, and a method for producing the hybrid ring-type smart stethoscope.

DISCLOSURE

Technical Problem

Accordingly, the present invention has been made in view of the above-mentioned problems occurring in the related art, and it is an object of the present invention to provide a hybrid ring-type smart stethoscope which can effectively auscultate a user's pulse and cardiopulmonary sounds, and is conveniently portable on an ordinary day, and a method for producing the same.

Technical Solution

To accomplish the above-mentioned objects, according to the present invention, there is provided a hybrid ring-type smart stethoscope including: a connection part which has a hollow hole into which a user's finger is inserted; an upper structure which is provided on the top of the connection part; and a lower structure which is provided on the bottom of the connection part, and has a measurement module collecting body-related information, which includes the user's heartbeat or respiratory information, by coming into contact with the user.

Moreover, coupling parts are respectively hinge-coupled to the upper structure and the lower structure, such that the upper structure and the lower structure rotate based on the coupling parts hinge-coupled to the connection part to adjust angles of the upper structure and the lower structure.

Here, the top of the connection part is coupled to the center of the bottom portion of the upper structure, and the lower end of the connection part is coupled to one end of the lower structure, such that when the hybrid ring-shaped smart stethoscope is unfolded, the overall shape of the hybrid ring-shaped smart stethoscope is formed in a " " shape.

Furthermore, when the hybrid ring-shaped smart stethoscope is returned, the upper structure rotates around the coupling part coupled to the connection part so that the connection part is accommodated in a first accommodation part having a depth to accommodate the connection part, and the lower structure rotates around the coupling part coupled to the connection part so that the connection part is accommodated in a second accommodation part having a depth to accommodate the connection part.

Additionally, the lower structure is provided to be detachable from the bottom portion of the connection part according to the user's manipulation, and on the bottom portion of the lower structure in which a measurement module is provided, an adhesive part is formed to form adhesive force by touching the user's skin.

In addition, the connection part further comprises a user pulse blocking means configured to absorb the user's pulse vibration transmitted through the user's finger inserted into the hollow hole, thereby reducing errors in a pulse measurement by the measurement module caused by the user's pulse vibration transferred through the user's finger, and the user pulse blocking means is formed to be detachably attached to the hollow hole into which the user's finger is inserted.

Moreover, the lower structure further comprises a separation detection sensor which derives separation information between the user's skin and the lower structure when the bottom portion of the lower structure having the measurement module is separated from the user's skin, and the connection part has the vibration module interworking with the separation detection sensor, such that the vibration module is vibrated based on the separation information derived from the separation detection sensor when detecting a distance between the lower structure and the user's skin.

Furthermore, the lower structure further comprises an anti-slip means which is provided at the bottom portion of the lower structure having the vibration module to prevent the lower structure from slipping on the user's skin, and the anti-slip means is formed on the surface where the lower structure gets in contact with the user's skin, and the cross-section of the lower structure has protrusions and recesses with uniform patterns.

In another aspect of the present invention, there is provided a method of producing a hybrid ring-shaped smart stethoscope including the steps of: preparing a connection part for wearing on a user's finger; installing an upper structure on the top of the connection part in a foldable manner; and installing a lower structure on the bottom of the connection part in a foldable manner.

In addition, the upper portion of the connection part is coupled to the middle of the bottom of the upper structure, and the bottom portion of the connection part is coupled to the end of the lower structure, such that when the hybrid ring-shaped smart stethoscope is unfolded, the overall shape of the hybrid ring-shaped smart stethoscope is formed in a " " shape.

Advantageous Effect

The hybrid ring-type smart stethoscope according to an embodiment of the present invention is provided in a ring-type that a user can wear, can effectively auscultate the user's pulse and cardiopulmonary sounds, and allows the user to carry the stethoscope conveniently on ordinary days.

Additionally, the hybrid ring-type smart stethoscope according to an embodiment of the present invention enables not only a user who directly uses the stethoscope but also a user who is far away to use.

In addition, the hybrid ring-type smart stethoscope according to the embodiment of the present invention is operated to, during the process of storing the user's examination results in a user server database, detect abnormal signs in the user's health status that were not previously detected, thereby allowing for more accurate diagnosis.

DESCRIPTION OF DRAWINGS

Figure 1:
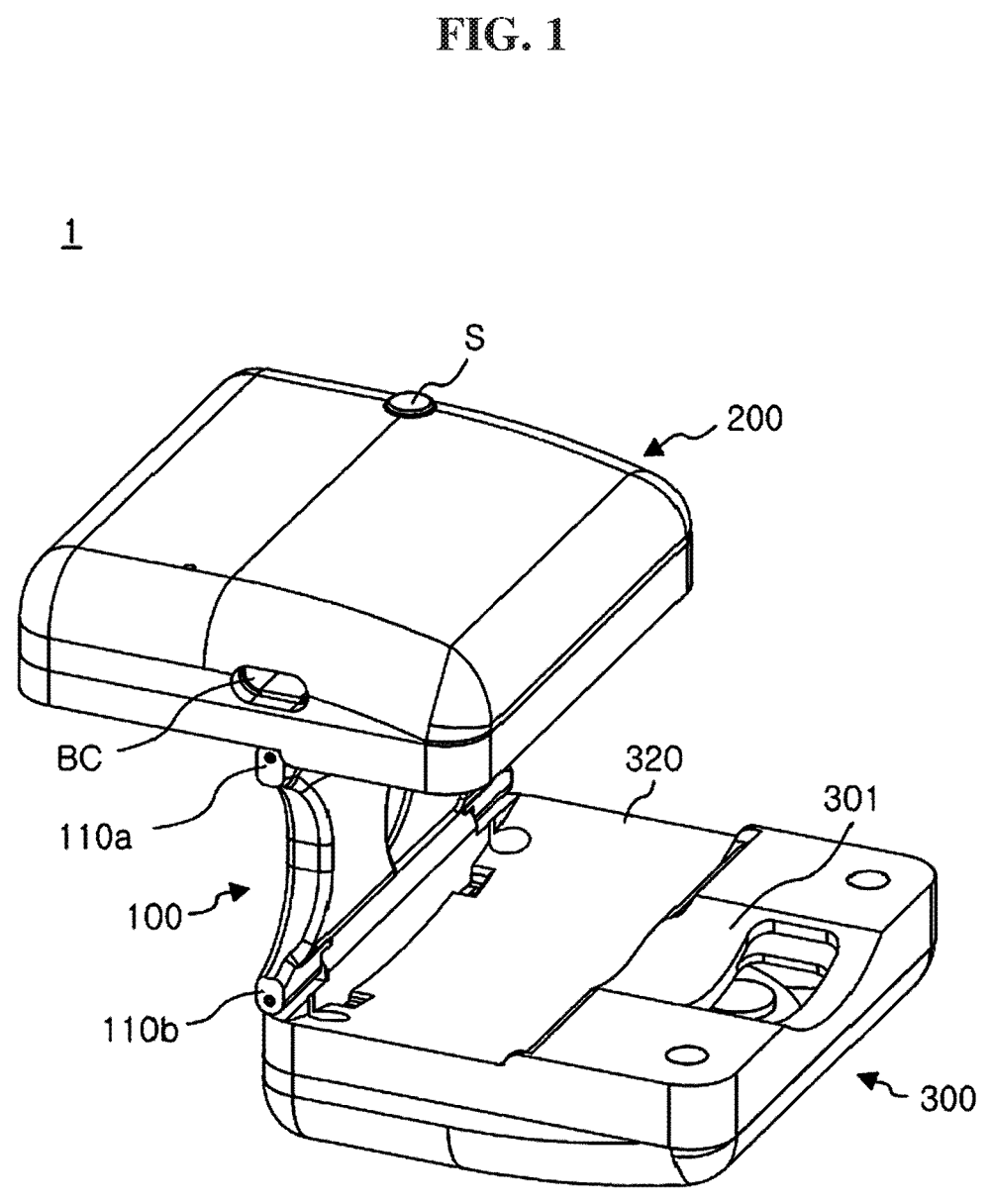

FIG. 1 is a perspective view of a hybrid ring-type smart stethoscope according to an embodiment of the present invention.

MODE FOR INVENTION

Figure 2:
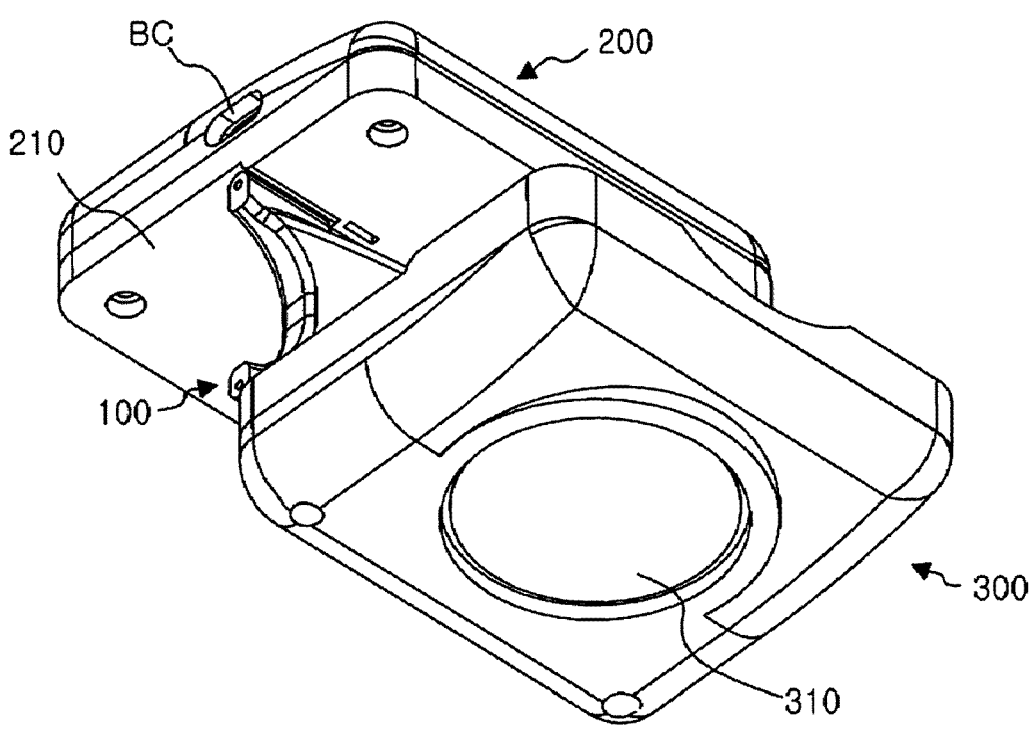
FIG. 2 is a bottom view of the hybrid ring-type smart stethoscope according to the embodiment of the present invention.

Hereinafter, with reference to the attached drawings, the present invention will be described in detail, but the present invention is not limited by specific embodiments, and can be modified in various forms and can have various embodiments. Moreover, it should be understood that the invention includes all modifications, equivalents, and replacements belonging to the concept and the technical scope of the invention.

In the following description, terms, such as "first" or "second" may be used to describe various components, but are not restricted to the above terms. The terms may be used to discriminate one component from another component.

Like reference numerals in the drawings denote like components.

The singular form of the components may be understood into the plural form unless otherwise specifically stated in the context. It should be also understood that the terms of 'include' or 'have' in the specification are used to mean that there are characteristics, numbers, steps, operations, components, parts, or combinations of the steps, operations, components and parts described in the specification and there is no intent to exclude existence or possibility of other characteristics, numbers, steps, operations, components, parts, or combinations of the steps, operations, components and parts.

In the meantime, not otherwise particularly defined, it will be understood that all terms used in the specification including technical or scientific terms has the same meanings as to be generally or commonly understood by those of ordinary skill in the art. It will be further understood that words or terms described as the meaning defined in commonly used dictionaries shall be interpreted as having meanings that are consistent with their meanings in the context of the relevant art and the technical idea of the invention, and shall not be interpreted as having ideal meanings or excessively formal meanings, not otherwise particularly stated.

Moreover, in describing the invention with reference to the accompanying drawings, like elements are referenced by like reference numerals or signs regardless of the drawing numbers and description thereof is not repeated. In the description, details of well-known features and techniques may be omitted to avoid unnecessarily obscuring the presented embodiments.

Hereinafter, referring to FIGS. 1 to 13, a hybrid ring-type smart stethoscope 1 and a method for producing the hybrid ring-type smart stethoscope 1 according to embodiments of the present invention will be described in detail.

Figure 3:
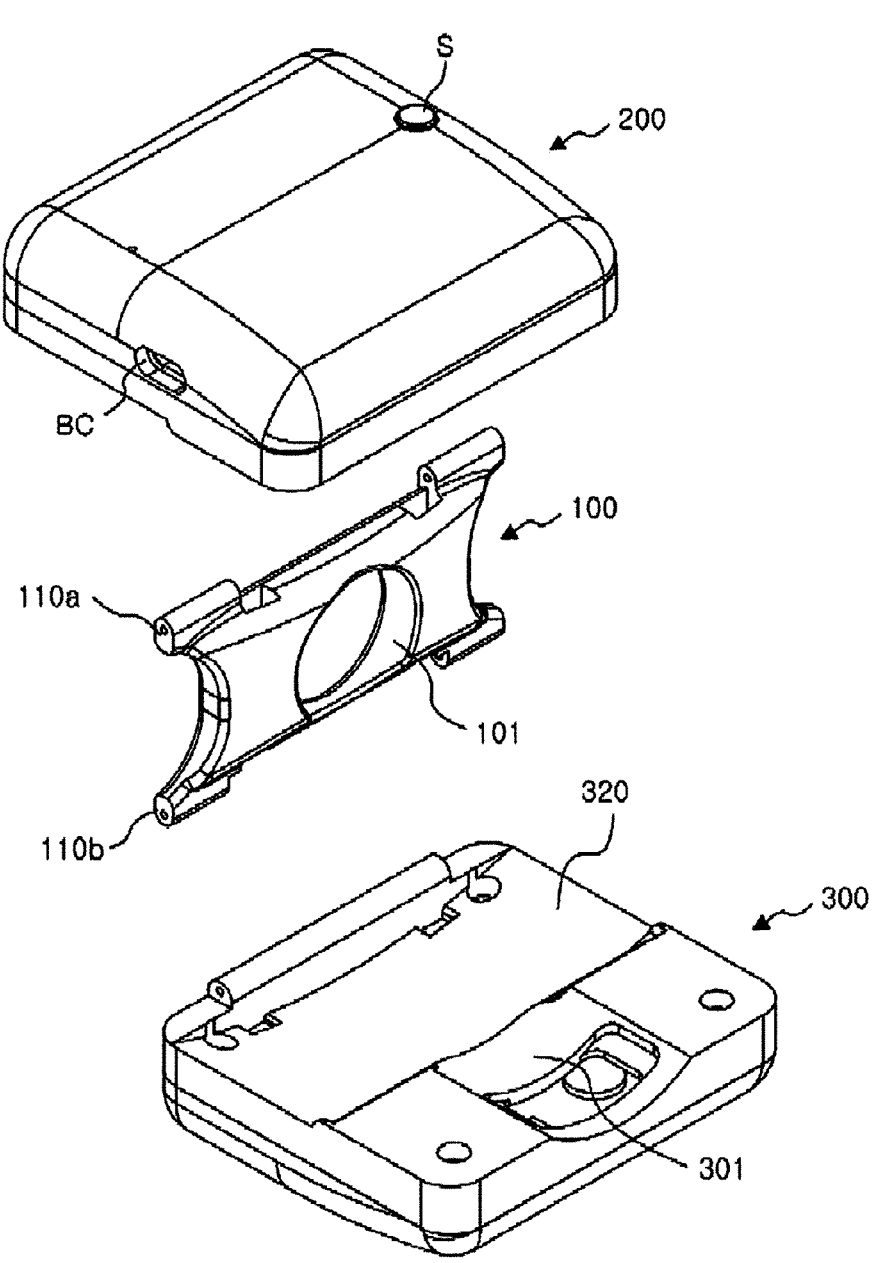
FIG. 3 is an exploded view of the hybrid ring-type smart stethoscope according to the embodiment of the present invention.
Figure 4:
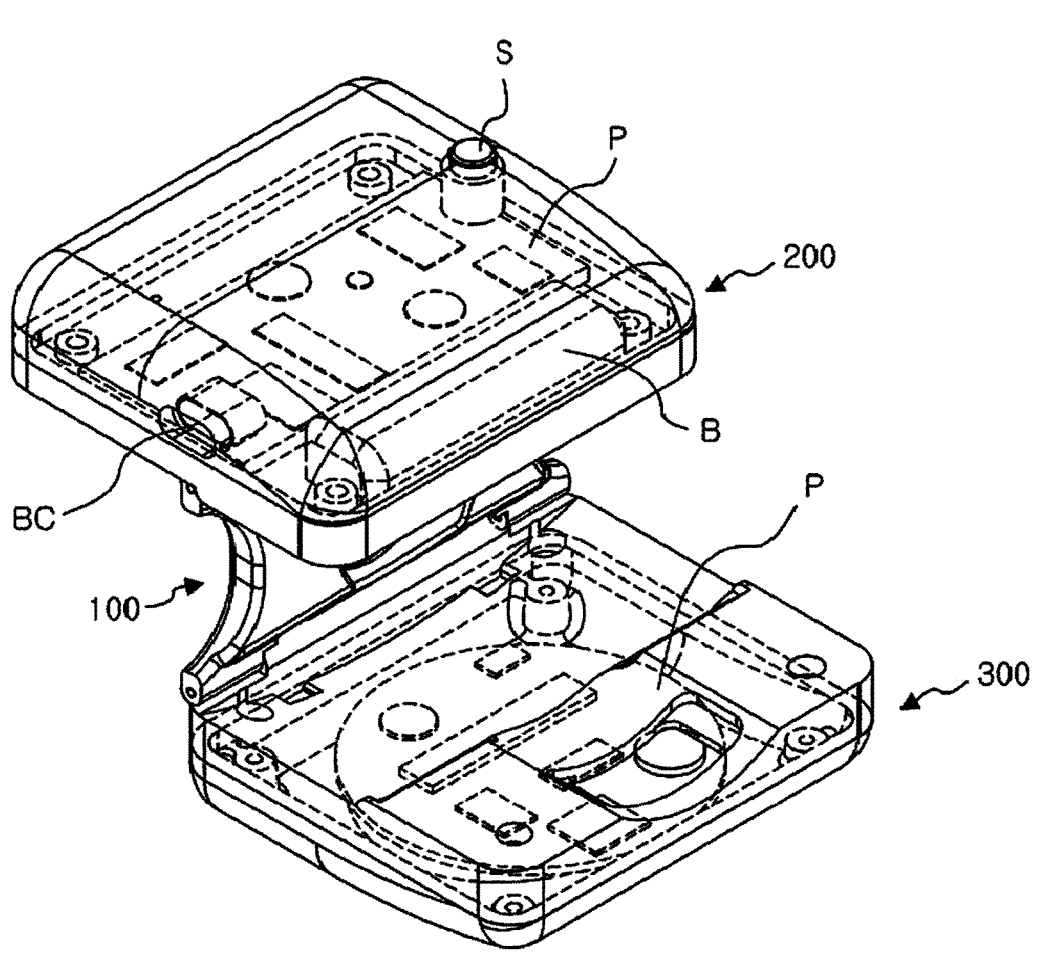
FIG. 4 is a projective view showing the components built in an upper structure and a lower structure of the present invention.
Figure 5:
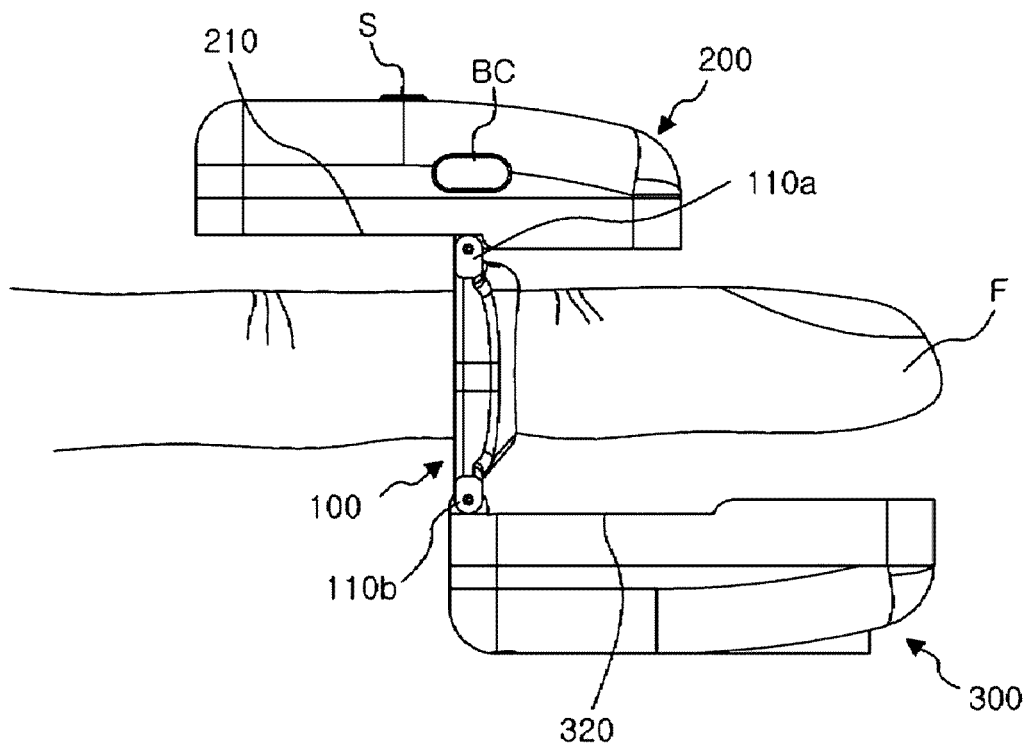
FIG. 5 is an exemplary view of the hybrid ring-type smart stethoscope worn on a user's finger.
Figure 6A:
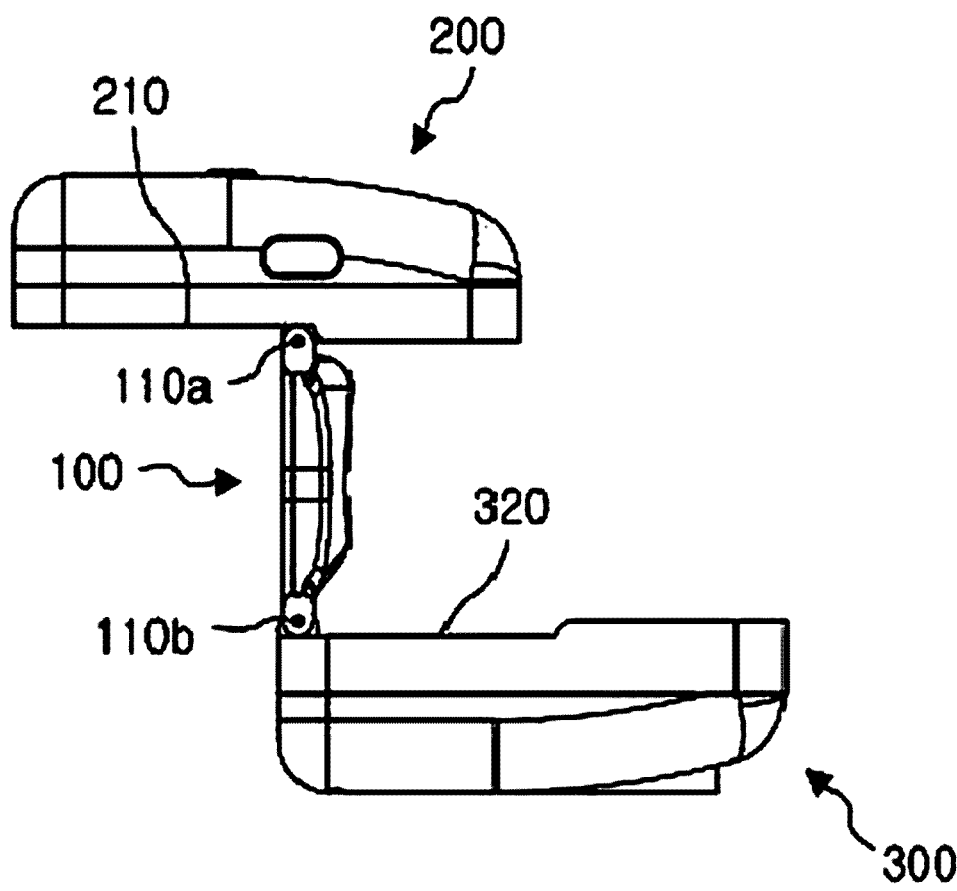
FIGS. 6A to 6C are operational example views showing how to unfold the hybrid ring-type smart stethoscope according to the embodiment of the present invention.
Figure 6B:
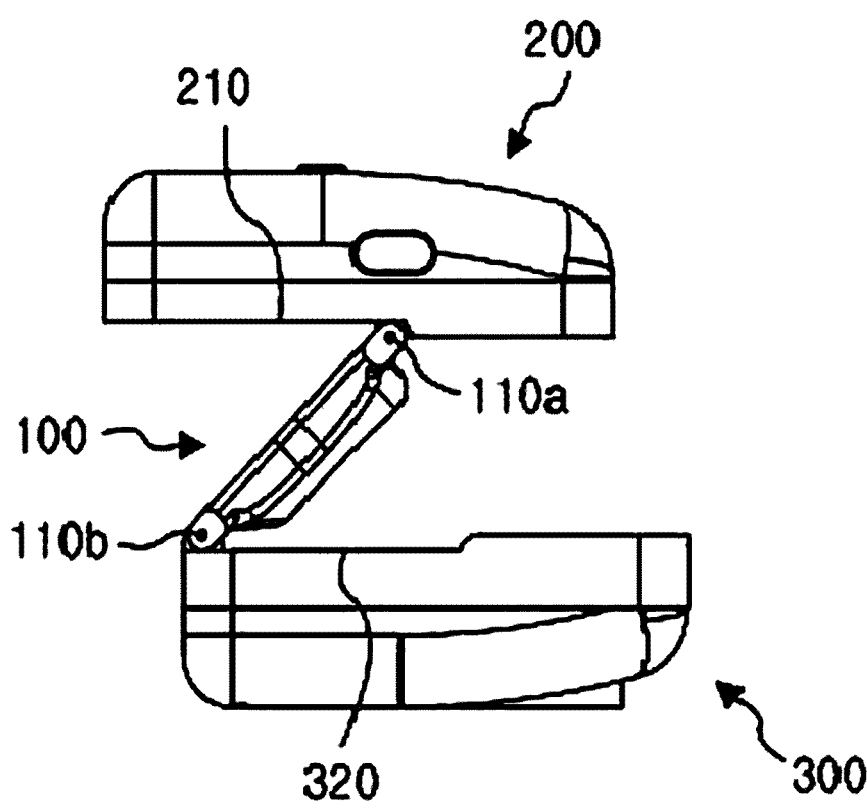
Figure 6C:
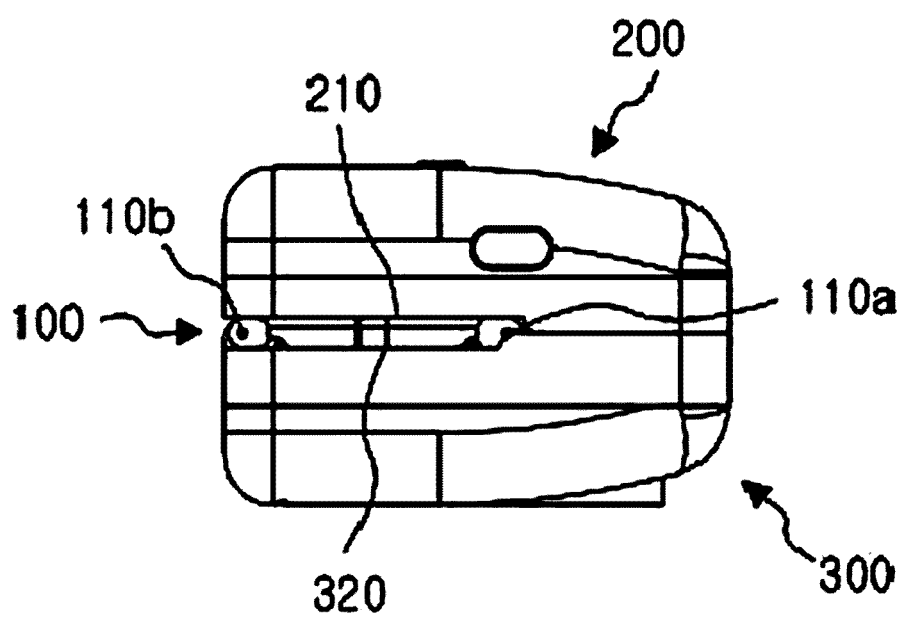

First, FIG. 1 is a perspective view of a hybrid ring-type smart stethoscope according to an embodiment of the present invention, FIG. 2 is a bottom view of the hybrid ring-type smart stethoscope according to the embodiment of the present invention, FIG. 3 is an exploded view of the hybrid ring-type smart stethoscope according to the embodiment of the present invention, FIG. 4 is a projective view showing the components built in an upper structure and a lower structure of the present invention, FIG. 5 is an exemplary view of the hybrid ring-type smart stethoscope worn on a user's finger, and FIGS. 6A to 6C are operational example views showing how to unfold the hybrid ring-type smart stethoscope according to the embodiment of the present invention.

Referring to FIGS. 1 to 6C, the hybrid ring-type smart stethoscope 1 according to an of the present invention includes a connection part 100, an upper structure 200, and a lower structure 300.

First, the connection part 100 has a hollow hole 101 into which a user's finger F can be inserted, and has the overall shape formed in a ring type.

Moreover, the upper structure 200 is provided on the top of the connection part 100, and has a shape corresponding to the top circumference of the user's finger F.

Furthermore, the upper structure 200 can include a battery B, a wireless charging coil, and a circuit board P which are provided to supply power to the measurement module 310 of the lower structure 300, which will be described in detail later.

Additionally, On the side surface or the rear surface of the upper structure 200, a wireless charging means BC based on a separate docking mechanism can be provided to charge the battery B housed within the upper structure 200.

In addition, on the upper structure 200, a switch S which can turn ON/OFF power of the hybrid ring-type smart stethoscope 1 can be provided.

Moreover, the lower structure 300 is provided at the lower portion of the connection part 100, and includes a curved portion 301 having a shape corresponding to the bottom surface of the user's finger F.

The measurement module 310 can be provided on the bottom portion of the lower structure 300 to collect body-related information including the user's heartbeat or cardio-pulmonary information by coming into contact with the user.

Here, the measurement module 310 can have an electrode sensor having a negative (–) polarity or a positive (+) polarity, or a pulse sensor capable of measuring blood flow changes caused by the user's heartbeat, and all sensors used to measure the user's bodily functions can be utilized.

The term "body-related information" may ideally refer to information related to the user's pulse or cardiopulmonary functions, which is the original purpose of the stethoscope, but may include all kinds of body-related information capable of being derived for the purpose of examining the user, such as body temperature or blood pressure.

Furthermore, the upper structure 200 and the lower structure 300 can be positioned on the connection part 100 in a horizontal direction state and be worn on the user's finger F.

Additionally, the upper structure 200 can be transformed from the horizontal direction state into a vertical direction state by rotating around a coupling part 110*a* coupled to the connection part 100.

In addition, the lower structure 300 can be transformed from the horizontal direction state into a vertical direction state by rotating around a coupling part 110*b* coupled to the connection part 100 in a state in which the user's finger F is removed from the connection part 100.

In this instance, to describe in more detail the manner in which the upper structure 200 and the lower structure 300 are unfolded from the connection part 100, referring to FIGS. 5 and 6, the present invention will be described in more detail.

First, the top of the connection part 100 can be coupled to the center of the bottom portion of the upper structure 200.

Moreover, the bottom side of the connection part 100 can be coupled to the top side of the lower structure 300, specifically, can be coupled to an edge of one side, in the longitudinal direction, of the lower structure 300, that is, an end of one side of the lower structure.

In other words, upon unfolding the hybrid ring-type smart stethoscope 1, the overall shape of the fully unfolded hybrid ring-type smart stethoscope 1 can be formed in a " " shape.

Moreover, a first accommodation part 210 for accommodating the connection part 100 can be formed at a lower portion of the upper structure 200, which is coupled to the connection part 100, when the upper structure 200 rotates around the coupling part 110*a* coupled to the connection part 100.

Furthermore, a second accommodation part 320 for accommodating the connection part 100 can be formed at an upper portion of the lower structure 300, which is coupled to the connection part 100, when the lower structure 300 rotates around the coupling part 110*b* coupled to the connection part 100.

The operation of the present invention will be described in detail. In a case in which, after measuring the heartbeat and cardiopulmonary information using the present invention and finishing the use of the present invention, a user wishes to restore the hybrid ring-type smart stethoscope 1 to the original state, the user can rotate the upper structure 200 and the lower structure 300 around the coupling parts 110*a* and 110*b* which are connected to the connection part 100. Thereafter, the user forcibly inserts the connection part 100 between the first accommodation part 210 and the second accommodation part 320, such that the shape of the hybrid ring-type smart stethoscope 1 is transformed into a box shape, thereby enabling the user to store the hybrid ring-type smart stethoscope 1 in the user's pocket or a case.

Accordingly, the hybrid ring-type smart stethoscope 1 according to an embodiment of the present invention can be fit onto the user's finger F by being unfolded when being used, and after the user, can be folded by the upper structure 200 and the lower structure 300 rotated in the direction of the connection part 100, thereby being stored and carried more easily.

Figure 7A:
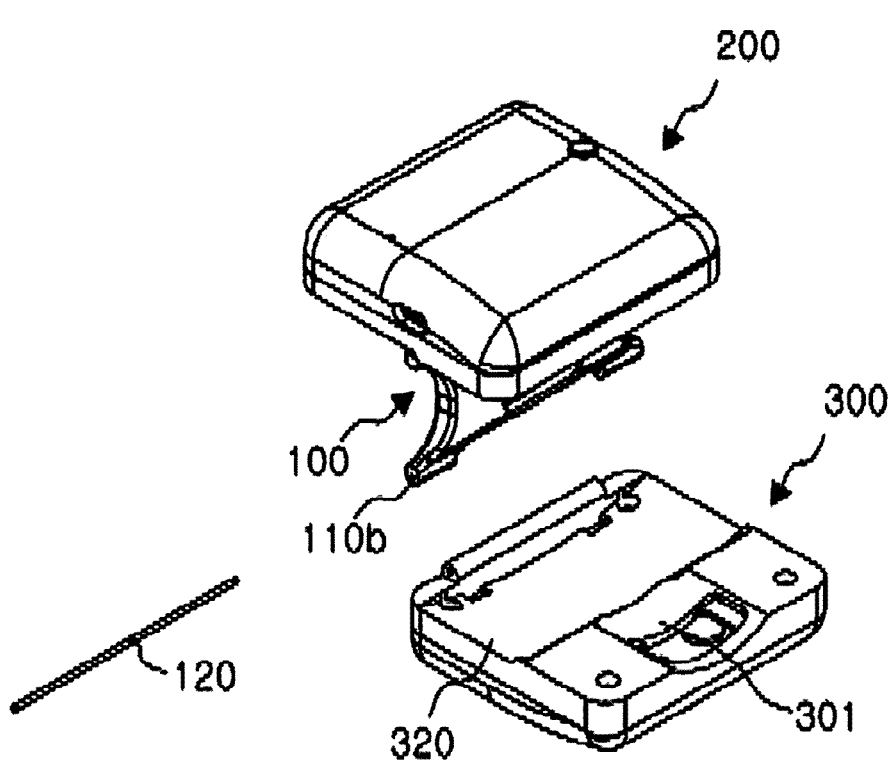
FIGS. 7A and 7B are exemplary views showing a lower structure which is detachably attached, and an adhesive part provided on the bottom surface of the lower structure according to the embodiment of the present invention.
Figure 7B:
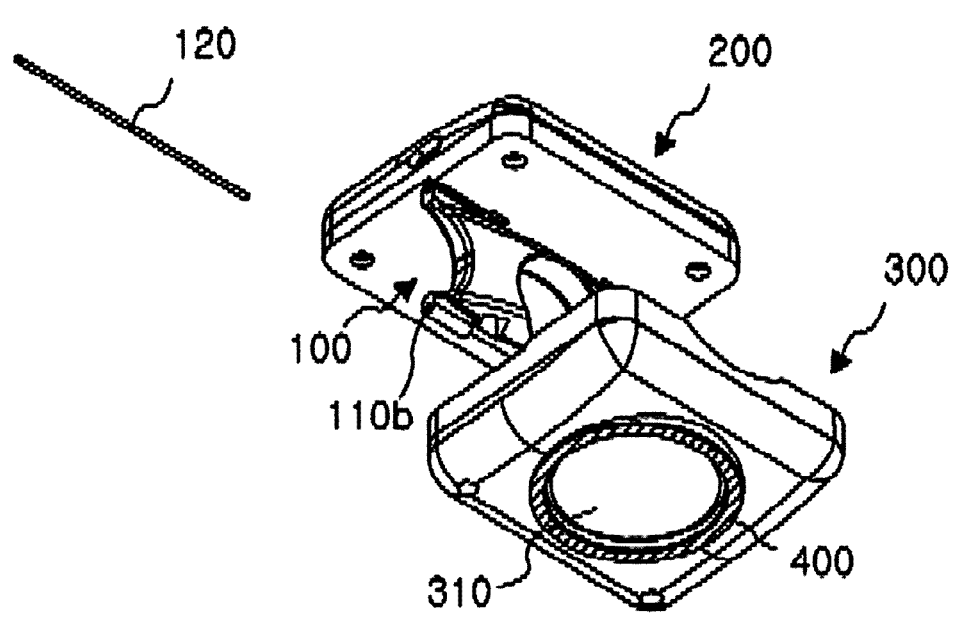

FIGS. 7A and 7B are exemplary views showing a lower structure which is detachably attached, and an adhesive part provided on the bottom surface of the lower structure according to the embodiment of the present invention.

Referring to FIGS. 7A and 7B, the lower structure 300 in accordance with the embodiment of the present invention can be provided to be detachably attached to the bottom portion of the connection part 100 depending on the user's manipulation.

In detail, the coupling part 100*b* which couples the lower structure 300 to the connection part 100 has a shaft 120 which is provided to be detached from the coupling part 100*b* and can restrict or disassemble the lower structure 300 from the connection part 100.

Additionally, the lower structure 300 may have an adhesive part 400 which can form adhesive force when coming into contact with the user's skin.

At this time, the adhesive part 400 can use a medical adhesive to form fixing force when coming into contact with the user's skin. Alternatively, the adhesive part 400 may have a Velcro fastener which can be attached and fixed to the surface of the user's outer skin, that is, the surface of the user's clothing.

Accordingly, the hybrid ring-type smart stethoscope 1 according to the embodiment of the present invention offers the advantage of allowing the user to adhere the lower structure 300 to another user's chest and transmit information remotely, thereby enabling remote examinations.

Figure 8:
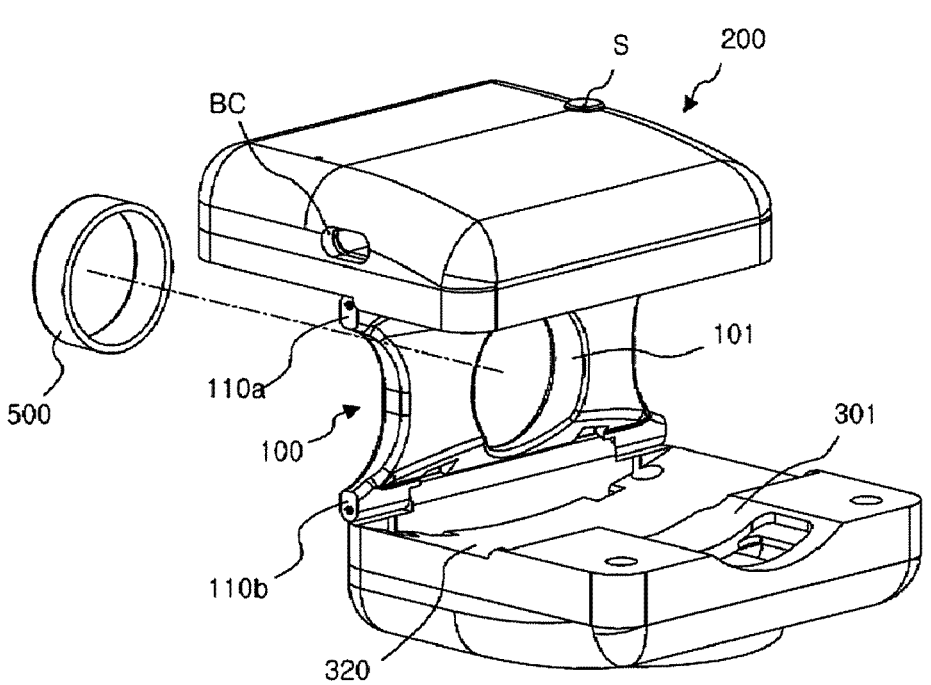
FIG. 8 is an exemplary view of a connection part where a user pulse blocking means is mounted.

Moreover, FIG. 8 is an exemplary view of a connection part where a user pulse blocking means is mounted.

Referring to FIG. 8, the connection part 100 according to the embodiment of the present invention can further include a user pulse blocking means 500 to reduce errors caused by the pulse transmitted through the user's finger F inserted into the hollow hole 101.

Specifically, the user pulse blocking means 500 is configured to block the user's pulse transmitted through the user's finger F inserted into the connection part 100. The user pulse blocking means 500 according to the embodiment of the present invention can be provided on the edge of the hollow hole 101 where the user's finger F is inserted.

More specifically, the user pulse blocking means 500 can be formed to be detachable from the hollow hole 101 according to the user's selection. As illustrated in FIG. 8, the user pulse blocking means 500 may be formed of a rubber packing material which can be detached from the hollow hole 101, but the rubber packing material is just a preferred embodiment, and a cushioning member directly installed on the edge of the rim of the hollow hole 101 can be used.

Therefore, the hybrid ring-shaped smart stethoscope 1 according to an embodiment of the present invention can reduce the possibility of errors in measuring the user's pulse due to the user's pulse vibration transferred through the user's finger F, thereby enabling more accurate measurement.

Figure 9:
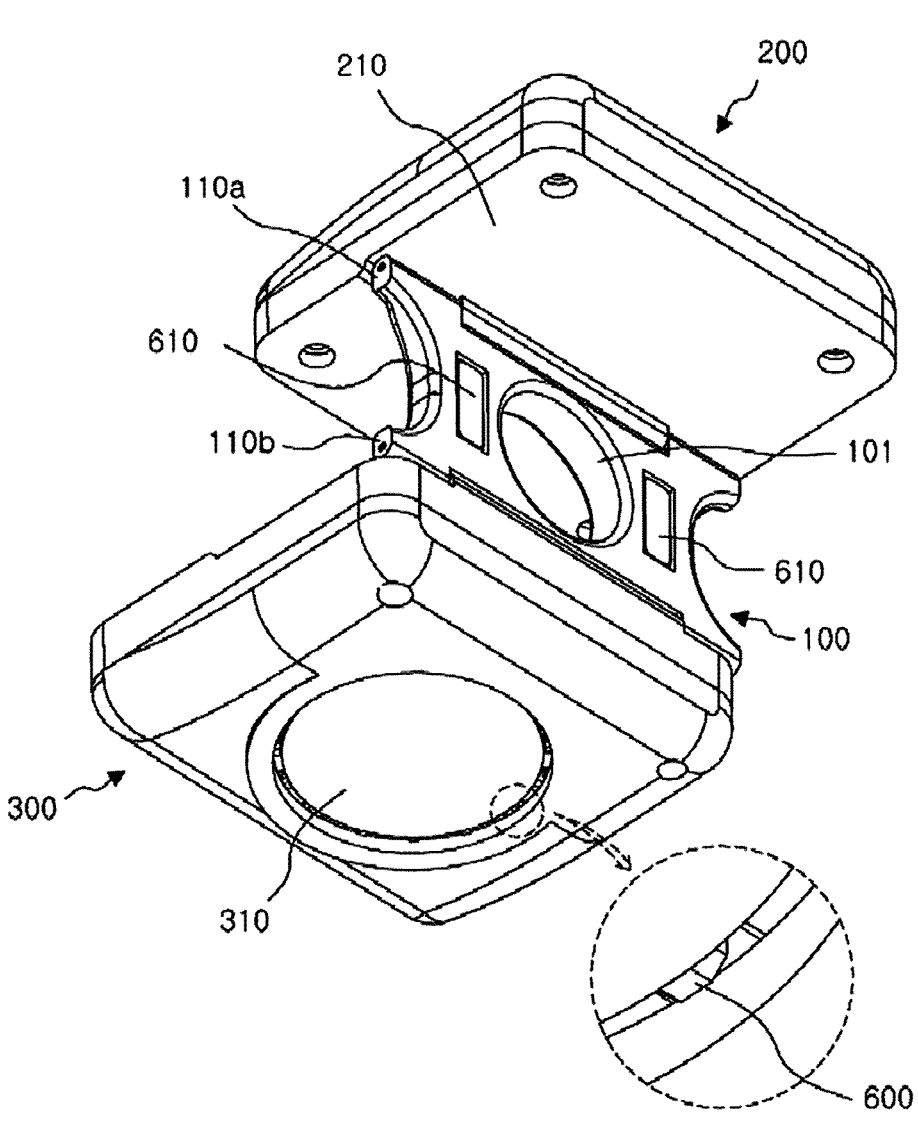
FIG. 9 is an exemplary view of a vibration module and a separation detection sensor of the hybrid ring-type smart stethoscope according to the embodiment of the present invention.

Additionally, FIG. 9 is an exemplary view of a vibration module and a separation detection sensor of the hybrid ring-type smart stethoscope according to the embodiment of the present invention.

Referring to FIG. 9, the lower structure 300 of the embodiment of the present invention can further include a separation detection sensor 600 which derives separation information between the user's skin and the separated lower structure 300 when the portion getting in contact with the user's skin becomes separated.

Furthermore, the connection part 100 can include vibration modules 610 interworking with the separation detection sensor 600.

Specifically, when the separation detection sensor 600 detects a separation distance between the lower structure 300 and the user's skin, the separation detection sensor 600 can send a signal to the vibration modules 610, such that the vibration modules 610 provided in the connection part 100 are vibrated.

Meanwhile, the vibration modules 610 are, preferably, as shown in FIG. 9, on both sides of the hollow hole 101 of the connection part 100. However, the location of the vibration modules 610 is to enable for the user to feel vibration of the vibration modules 610 surely, and is not limited thereto, so, the vibration modules 610 may be provided in the connection part 100, the upper structure 200, the lower structure 300, or a user terminal 800 which will be described later.

Therefore, the hybrid ring-shaped smart stethoscope 1 according to the embodiment of the present invention can overcome the problem of not being able to make an accurate diagnosis due to improper contact of the lower structure 300 of the hybrid ring-shaped smart stethoscope 1 when the user performs an examination.

Figure 10:
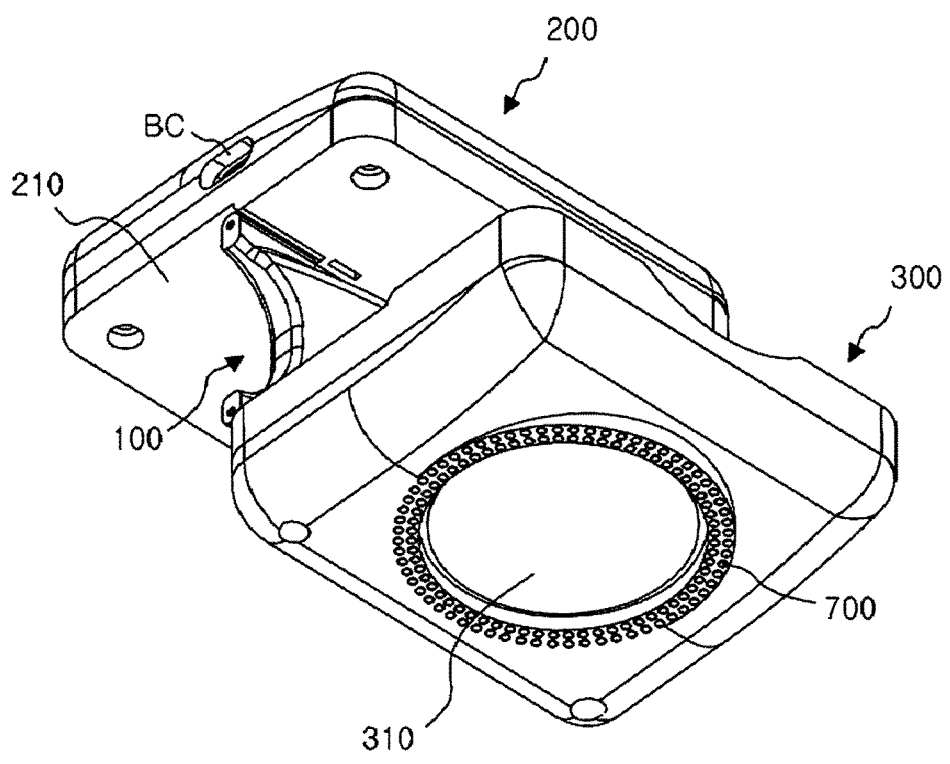
FIG. 10 is a bottom view of the lower structure having an anti-slip means.

In addition, FIG. 10 is a bottom view of the lower structure having an anti-slip means.

Referring to FIG. 10, the hybrid ring-shaped smart stethoscope 1 according to an embodiment of the present invention can further include an anti-slip means 700 to prevent the lower structure 300 from slipping on the user's skin in contact with the measurement module 310.

Specifically, the anti-slip means 700 can be formed on one side which comes into contact with the user's skin, and the most preferably, is formed on the bottom portion of the lower structure 300 where the measurement module 310 is mounted.

At this time, the anti-slip means 700, as illustrated in FIG. 10, can be formed to have protruding patterns arranged at regular intervals on the surface of the lower structure 300, and may be made of a material having appropriate frictional resistance coefficients, such as synthetic rubber.

Therefore, the hybrid ring-shaped smart stethoscope 1 according to the embodiment of the present invention can overcome the problem occurring due to slipping of the lower structure 300, which is in contact with the user's skin, on the surface of the user's skin.

Figure 11:
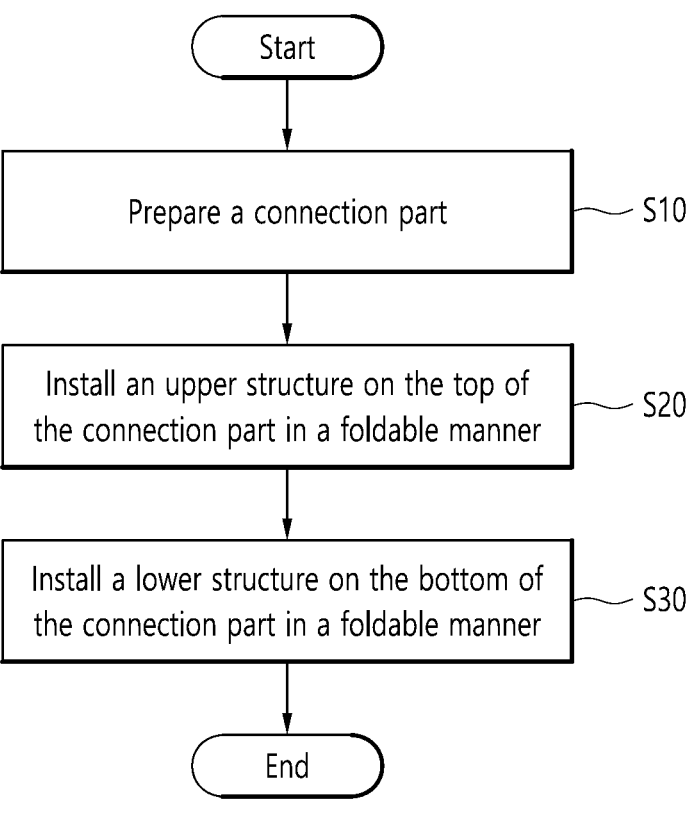
FIG. 11 is a flowchart of a method for producing a hybrid ring-type smart stethoscope according to an embodiment of the present invention.

Furthermore, FIG. 11 is a flowchart of a method for producing a hybrid ring-type smart stethoscope according to an embodiment of the present invention.

Referring to FIG. 11, a method for producing the hybrid ring-type smart stethoscope according to the embodiment of the present invention will be described in detail. The method for producing the hybrid ring-type smart stethoscope includes: a step (S10) of preparing a connection part for wearing on a user's finger; a step (S20) of installing an upper structure on the top of the connection part in a foldable manner; and a step (S30) of installing a lower structure on the bottom of the connection part in a foldable manner.

Here, a curved portion 301 having a shape corresponding to the bottom surface of the user's finger may be formed on the side where the upper structure and the lower structure touch the user's finger.

On the other hand, the top of the connection part is joined to the middle bottom of the upper structure, and the lower portion of the connection part is joined to the end of the lower structure. Thus, when the hybrid ring-type smart stethoscope is unfolded, the overall shape of the fully unfolded hybrid ring-type smart stethoscope 1 can be formed in a " ⌐‿⌐ " shape.

As a result, the hybrid ring-type smart stethoscope manufactured by the method according to the embodiment of the present invention can be unfolded and worn on the user's finger when in use. After an examination, the upper structure and the lower structure can be rotated in the direction of the connection part to be folded, thereby allowing for more convenient storage and carrying.

Figure 12:
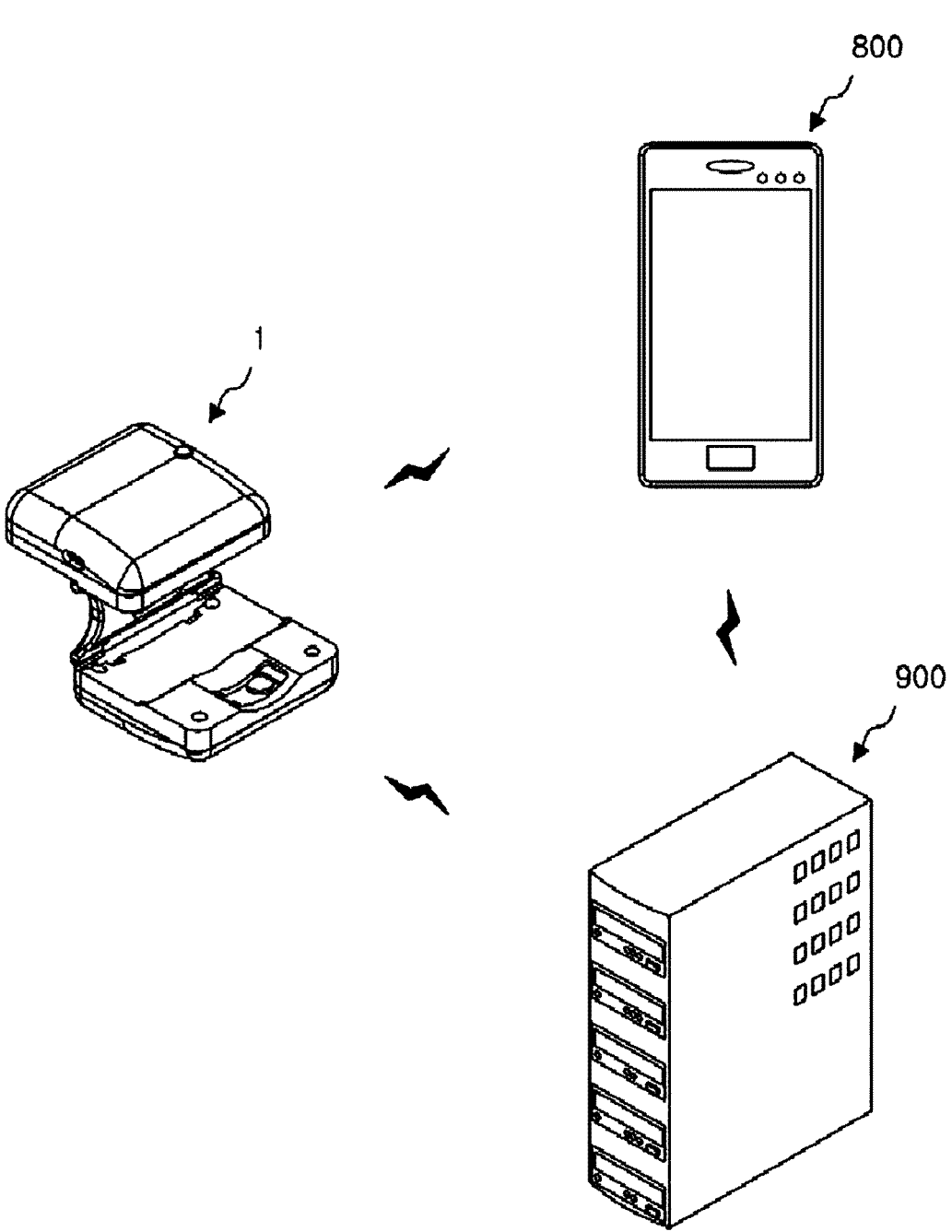
FIG. 12 is a configuration diagram of a measurement system using the hybrid ring-type smart stethoscope according to an embodiment of the present invention.
Figure 13:
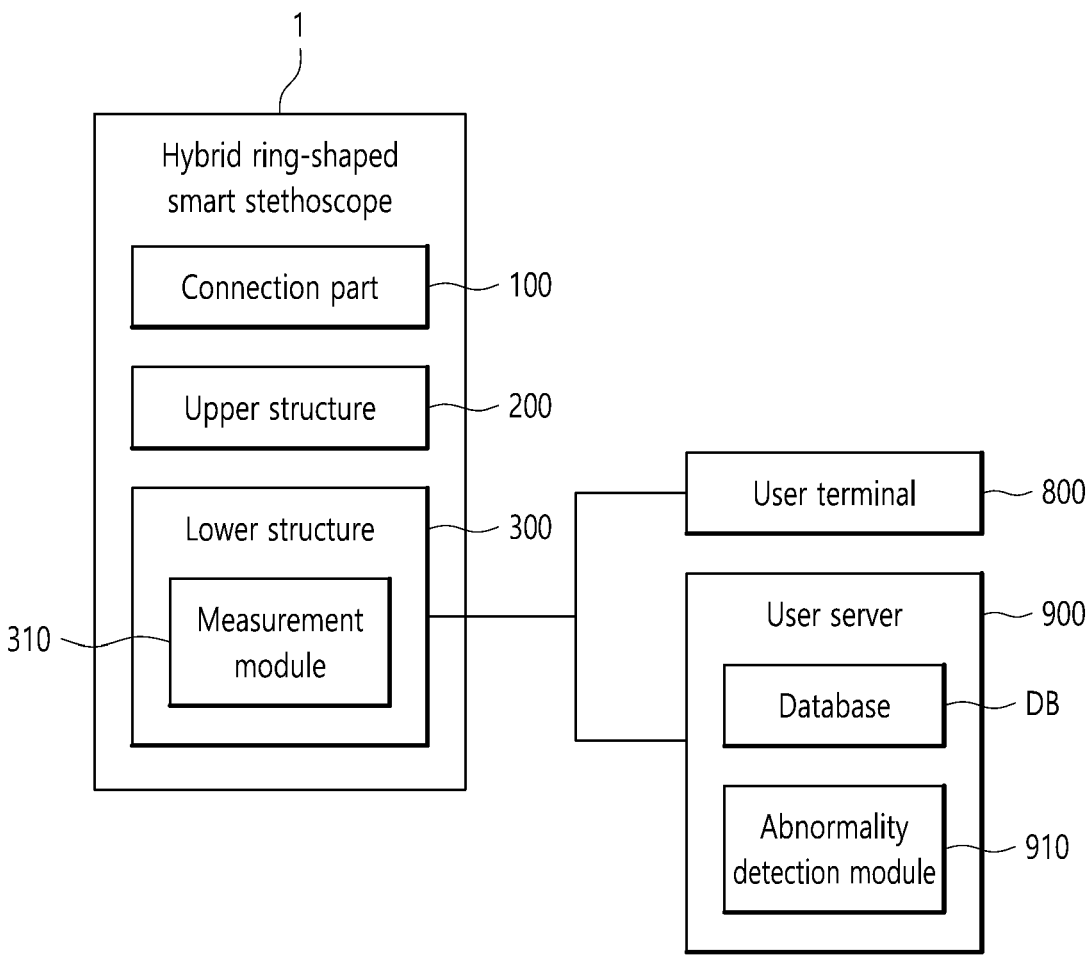
FIG. 13 is a block diagram showing a systematic configuration of a measurement system using the hybrid ring-type smart stethoscope according to an embodiment of the present invention.

Finally, FIG. 12 is a configuration diagram of a measurement system using the hybrid ring-type smart stethoscope according to an embodiment of the present invention, and FIG. 13 is a block diagram showing a systematic configuration of a measurement system using the hybrid ring-type smart stethoscope according to an embodiment of the present invention.

Referring to FIGS. 12 and 13, the measurement system using the hybrid ring-type smart stethoscope 1 having the measurement module 310, which collects body-related information including the user's heartbeat or cardiopulmonary information by being in contact with the user, can include a user terminal 800 and a user server 900.

Firstly, the user terminal 800 can be configured to send and receive the user's body-related information measured through the measurement module 310 of the hybrid ring-type smart stethoscope 1 by interworking with the hybrid ring-type smart stethoscope 1.

Here, the user terminal 800 has a display which allows the user to visually check the body-related information. As a result, the body-related information derived from the hybrid ring-type smart stethoscope 1 can be graphically displayed to the user.

Moreover, the user server 900 can interwork with the hybrid ring-type smart stethoscope 1 or the user terminal 800 which the user might have, and can communicate with the hybrid ring-type smart stethoscope 1 to send and receive data.

Furthermore, the user server 900 may have a database DB constructed to receive and store examination information transmitted from the hybrid ring-shaped smart stethoscope 1.

Here, the user terminal 800 can access the database DB constructed in the user server 900 and read the user's body-related information stored in the database DB.

Therefore, the hybrid ring-shaped smart stethoscope 1 according to the exemplary embodiment of the present invention enables not only a user who directly uses the stethoscope but also a user who is far away to perform accurate examination based on the user's body-related information.

Additionally, the user server 900 according to the exemplary embodiment of the present invention can have an abnormality detection module 910 which detects user anomalies based on the body-related information stored in the database DB.

Specifically, the abnormality detection module 910 can be constructed to interface with a cloud which stores heartbeat patterns or cardiopulmonary patterns of a patient with a cardiovascular or pulmonary disease. The abnormality detection module 910, can continuously monitor the user's body-related information stored in the database DB of the user server 900 in real-time, and when a cloud interworking with the abnormality detection module 910 detects body-related information with similarity from the stored body-related information, can send a notification of the detected abnormalities to the user terminal 800 and transmit information about the disease name of a patient showing similar results for cardiovascular or pulmonary diseases to the user terminal 800.

Therefore, during a process of receiving the user's heartbeat or respiratory information and storing them in the database DB, the user server 900 of the hybrid ring-shaped smart stethoscope 1 according to the embodiment of the present invention can capture unnoticed anomalies of the user while the user examines another user and inform the result, thereby enabling a more accurate diagnosis of a patient.

As described above, with reference to FIGS. 1 through 13, the hybrid ring-shaped smart stethoscope 1 and the method for producing the same according to the embodiments of the present invention can be realized not only through devices and/or methods, but also through programs to realize functions corresponding to the configuration of the exemplary embodiment of the invention, and recording media on which the programs are recorded, etc., and the above can be easily realized by those skilled in the technical field from the above-described embodiment.

Moreover, although the exemplary embodiment of the invention has been described in detail above, the scope of the rights of the present invention is not limited thereto, and various modifications and improved forms using the basic concept of the present invention defined in the following claims also fall within the scope of the rights of the present invention.

---
Explanation of Reference Numerals
---

1: hybrid ring-shaped smart stethoscope
100: connection part
110: coupling part
200: upper structure
300: lower structure
310: measurement module
400: adhesive part
600: separation detection sensor
700: anti-slip means
900: user server
F: user finger
P: circuit board
S: switch 101: hollow hole
120: shaft
210: first accommodation part
301: curved portion
320: second accommodation part
500: user pulse blocking means
610 vibration module
800: user terminal
910: abnormality detection module
B: battery
BC: wireless charging means
DB: database

The invention claimed is:
1. A hybrid ring-shaped smart stethoscope comprising:
a connection part having:
a hollow hole configured to accommodate a finger of a user,
a first end,
a second end opposite the first end,
a first coupling portion disposed on the first end, and a second coupling portion disposed on the second end;
a first structure coupled to the first coupling portion of the connection part; and
a second structure detachably coupled to the second coupling portion of the connection part,
wherein a first accommodation portion configured to accommodate at least one portion of the connection part is defined in one surface of the first structure, the first accommodation portion extending from a location coupled to the first coupling portion of the connection part and having a first depth corresponding to a shape of the at least one portion of the connection part,
wherein a second accommodation portion configured to accommodate at least another portion of the connection part is defined in one surface of the second structure, the second accommodation portion extending from a location coupled to the second coupling portion of the connection part and having a second depth corresponding to a shape of the at least another portion of the connection part,
wherein the first accommodation portion and the second accommodation portion are parallel to each other,
wherein, when the hybrid ring-shaped smart stethoscope is returned to a folded state, the connection part is forcibly inserted and stored between the first accommodation portion and the second accommodation portion, and the first accommodation portion and the second accommodation portion together fully accommodate an entire connection part,
wherein the second structure includes a measurement module configured to be in contact with the user and collect body-related information, the body-related information including a heartbeat of the user or respiratory information, and
wherein the measurement module disposed on another surface of the second structure opposite the one surface on which the second accommodation portion is defined.
2. The hybrid ring-shaped smart stethoscope of claim 1, wherein the first coupling portion and the second coupling portion are hinge-coupled to the first structure and the second structure, respectively, and the first structure and the second structure rotate based on the hinge-coupling of the respective coupling portions of the connection part to adjust angles of the first structure and the second structure.
3. The hybrid ring-shaped smart stethoscope of claim 2, wherein
the first end of the connection part is coupled to a center of a bottom portion of the first structure, and
the second end of the connection part is coupled to one end of the second structure.
4. The hybrid ring-shaped smart stethoscope of claim 3, wherein when the hybrid ring-shaped smart stethoscope is in an unfolded state, the first structure and the second structure are parallel to each other and the connection part is perpendicular to the first structure and the second structure.
5. The hybrid ring-shaped smart stethoscope of claim 3, wherein when the hybrid ring-shaped smart stethoscope is returned to the folded state, the first structure rotates around the first coupling portion of the connection part and the connection part is accommodated in the first accommodation portion of the first structure, and
wherein the second structure rotates around the second coupling portion of the connection part and the connection part is accommodated in the second accommodation portion of the second structure.

6. The hybrid ring-shaped smart stethoscope of claim 1, wherein an adhesive portion is disposed on the another surface of the second structure to provide adhesive force by touching a skin of the user.

7. The hybrid ring-shaped smart stethoscope of claim 1, wherein the connection part further comprises a user pulse blocking member configured to absorb user's pulse vibration transmitted through a user's finger inserted into the hollow hole, thereby reducing errors in a pulse measurement by the measurement module caused by the user's pulse vibration transferred through the user's finger, and wherein the user pulse blocking member is detachably to the hollow hole configured to accommodate the user's finger.

8. The hybrid ring-shaped smart stethoscope of claim 1, wherein the second structure further comprises a separation detection sensor configured to derive separation information between a skin of the user and the second structure when the second structure having the measurement module is separated from the skin of the user, and wherein the connection part further comprises at least one vibration module interworking with the separation detection sensor, and the at least one vibration module is vibrated based on the separation information derived from the separation detection sensor when detecting a separation distance between the second structure and the skin of the user.

9. The hybrid ring-shaped smart stethoscope of claim 8, wherein the at least one vibration module includes two vibration modules respectively disposed on two opposing sides of the hollow hole defined in the connection part.

10. The hybrid ring-shaped smart stethoscope of claim 8, wherein the separation detection sensor is disposed on the another surface of the second structure directly adjacent to the measurement module.

11. The hybrid ring-shaped smart stethoscope of claim 1, wherein the second structure further comprises an anti-slip structure provided at the another surface of the second structure having at least one vibration module to prevent the second structure from slipping on a skin of the user, and wherein the anti-slip structure is disposed on the another surface of the second structure where the second structure is configured to contact with the skin of the user, and a cross-section of the second structure has protrusions and recesses with uniform patterns.

12. The hybrid ring-shaped smart stethoscope of claim 1, wherein the first accommodation portion and the second accommodation portion each have a length and a width corresponding to a length and a width of the connection part.

13. The hybrid ring-shaped smart stethoscope of claim 1, wherein a measurement module accommodation hole configured to accommodate the measurement module is defined in the another surface of the second structure, the measurement module accommodation hole having a shape corresponding to a shape of the measurement module.

14. The hybrid ring-shaped smart stethoscope of claim 1, wherein a curved portion having a shape corresponding to a bottom surface of the user's finger is defined in the one surface of the second structure.

15. A method of producing a hybrid ring-shaped smart stethoscope, the method comprising:

preparing a connection part configured to be worn on a user's finger, the connection part including:

a hollow hole configured to accommodate the user's finger, a first end, a second end opposite the first end, a first coupling portion disposed on the first end, and a second coupling portion disposed on the second end;

installing a first structure on the first end of the connection part in a foldable manner by coupling the first structure to the first coupling portion of the connection part; and installing a second structure on the second end of the connection part in the foldable manner by detachably coupling the second structure to the second coupling portion of the connection part, wherein a first accommodation portion configured to accommodate at least one portion of the connection part is defined in one surface of the first structure, the first accommodation portion extending from a location coupled to the first coupling portion of the connection part and having a first depth corresponding to a shape of the at least one portion of the connection part, wherein a second accommodation portion configured to accommodate at least another portion of the connection part is defined in one surface of the second structure, the second accommodation portion extending from a location coupled to the second coupling portion of the connection part and having a second depth corresponding to a shape of the at least another portion of the connection part, wherein the first accommodation portion and the second accommodation portion are parallel to each other, wherein, when the hybrid ring-shaped smart stethoscope is returned to a folded state, the connection part is forcibly inserted and stored between the first accommodation portion and the second accommodation portion, and the first accommodation portion and the second accommodation portion together fully accommodate an entire connection part, wherein the second structure includes a measurement module configured to be in contact with the user and collect body-related information, the body-related information including a heartbeat of the user or respiratory information, and wherein the measurement module disposed on another surface of the second structure opposite the one surface on which the second accommodation portion is defined.

16. The method of claim 15, wherein the first end of the connection part is coupled to a center of a bottom portion of the first structure, and the second end of the connection part is coupled to one end of the second structure.

17. The method of claim 16, wherein when the hybrid ring-shaped smart stethoscope is in an unfolded state, the first structure and the second structure are parallel to each other and the connection part is perpendicular to the first structure and the second structure.

* * * * *